United States Patent [19]

Meredith et al.

[11] Plant 4,597

[45] Sep. 30, 1980

[54] MINIATURE ROSE PLANT

[76] Inventors: Earnest A. Meredith; Margaret E. Rovinski, both of 12757 Barrett La., Santa Ana, Calif. 92705

[21] Appl. No.: 46,853

[22] Filed: Jun. 8, 1979

[51] Int. Cl.[3] ..... A01H 5/00

[52] U.S. Cl. ..... Plt./7

[58] Field of Search ..... Plt./7

*Primary Examiner*—Robert E. Bagwill

[57] ABSTRACT

The subject of the present disclosure is a new and distinct variety of miniature rose plant characterized primarily by the hybrid tea type, bi-color buds and flowers, basically white with deep Rose Bengal edges; the red coloring blending into the white area on the upper surface of the petals, but remaining essentially white with a distinct red edging.

6 Drawing Figures

The present invention relates to a new and distinct variety of dwarf, hardy, bush type rose plant of the miniature class; the variety being primarily characterized by its bi-colored buds and flowers; white petals with a distinct edging of Rose Bengal #25 (Wilson's Horticultural Color Chart).

This variety is further characterized by:

An abundance of bloom; usually born singly, but at times in loose clusters of several blooms.

Little or no fragrance.

The plant is vigorous, hardy; of upright growth and well clothed bush; semi-gloss leaves; normal height 14 to 18 inches.

This plant grows well in both greenhouse and out of doors; is good for pot culture; is an excellant garden decoration and provides cut flowers.

This variety of miniature rose was originated by us at Casa de Rosa Domingo nursery, located at Santa Ana, Calif., under conditions of careful control.

Seed parent: The hybrid tea Overture.
Pollen parent: Miniature rose Perla de Alcanada.

After testing the seedling we have successfully asexually reproduced it at Casa de Rosa Domingo nursery by budding and from cuttings. It has remained true in color and form in all propagation.

The color photographs illustrate the variety including the foliage, buds and all stages of flower.

The following is a detailed description of this new variety; all major color plate identifications being by reference to the Wilson Horticultural Color Chart, except where common terms of color definition are used.

Type: Hardy; vigorous; erect; dwarf; seeding; greenhouse; garden decorations; cut flowers; potted plant.

Class: Miniature.

*Variety name.*—Libby.

Flowers borne: Usually singly on slender but sturdy stems. At times, loose clusters of 3 to 6.

Quantity of bloom: Almost continuous, both outside and in the greenhouse.

Bud:

*Peduncle.*—Medium length, slender but sturdy; erect; medium green (at times tinged reddish); a few very short hairs.

*Calyx (before it breaks).*—Size, small; form, long; pointed with a few very short hairs; a few pointed, narrow foliaceous appendages on surface of bud; pointed sepals extending beyond the tip of the bud to one-third of bud's length. Color, medium green.

*Calyx (as it breaks).*—Deep Rose Bengal #25; as sepals drop, the white of the main portion of the petals becomes visible; opens well in all weather.

Bloom:

*Size when fully open.*—Small, averaging 1½"; 14 to 20 petals plus at times several petaloids. Classed as semi-double.

*Form.*—High centered to flat open with stamens showing. Petals symmetrically arranged, reflexing outwards to form a typical hybrid tea shaped bloom.

Petals: Fairly thick, with good substance; velvety, on inside and outside surfaces.

*Shape.*—Broad obovate in all rows of petals. Petaloids much more narrow.

Color: Newly opened flower from plant grown indoors (May 1978) Santa Ana, Calif.; flowers grown outdoors follow the same color pattern. All rows of petals follow the same color patterning.

*Outside surface.*—White or near white on entire surface with an edge or border of Rose Bengal #25.

*Inside surface.*—White or near white; Rose Bengal #25 edges; the red coloring blending into the white area, but remaining essentially white with a distinct red edging to the outer ¼ to ⅓ of the petals.

General color effect of newly opened flower: White with petal edges colored a bright contrasting shade of red.

Three days open: Same effect, but edging slightly lighter in color.

Behavior: Spent blooms drop cleanly; opens well in all weather.

Flower longevity: (May 1978) bush or pot 5–7 days; cut flowers at living room temperature (without refrigeration for hardening) 3–5 days.

Reproductive organs:

*Stamens.*—Abundant, arranged regularly around pistils.

*Filaments.*—Varying lengths, medium to long, yellow.

*Anthers.*—Well formed, yellow.

*Pistils.*—Average number.

*Stigmas.*—Pale greenish.

*Ovaries.*—Enclosed in calyx.

*Heps.*—Some.

*Seed.*—1-5 per hep, viable.

Foliage:

*Leaves.*—Compound, five leaflets. Size, medium. Leathery, glossy.

*Leaflets.*—Shape; elliptic, acute apex, margin serrate.

*Color.*—Glossy, medium green; new growth normally has reddish or bronze tint.

*Rachis.*—Medium strength; upper side has a few minute hairs; grooved; underside has a few small hooked thorns and tiny hairs.

*Stipules.*—Medium long; narrow to medium width; points are short and narrow, and normally turn out at about 45 degrees.

Growth:

*Habit.*—Dwarf, bushy, upright, well branched.

*Growth.*—Free, vigorous; internodes medium.

*Main stems.*—Color — medium green; thorns — few, triangular, downward pointing, reddish brown; prickles — few or none; hairs — none.

*Branches.*—Color — medium green; thorns — few, triangular, downward pointing, reddish brown; prickles — few or none; hairs — none.

*New growth.*—Color — reddish green or bronze.

The miniature rose plant and its flowers as herein described may vary in slight detail due to climatic, soil and cultural conditions under which the variety may be grown; the present description being of the variety as grown at Casa de Rosa Domingo nursery, Santa Ana, Calif.

The following is claimed:

1. A new and distinct variety of miniature rose plant, of hardy, dwarf, erect, well branched habit; substantially as illustrated and described herein; characterized by a flower basically white with a distinct red border or edging; further characterized by its bush — dwarf, erect, well branched, easy to propagate from cuttings or by budding; an abundance of flowers, borne singly or in loose clusters.

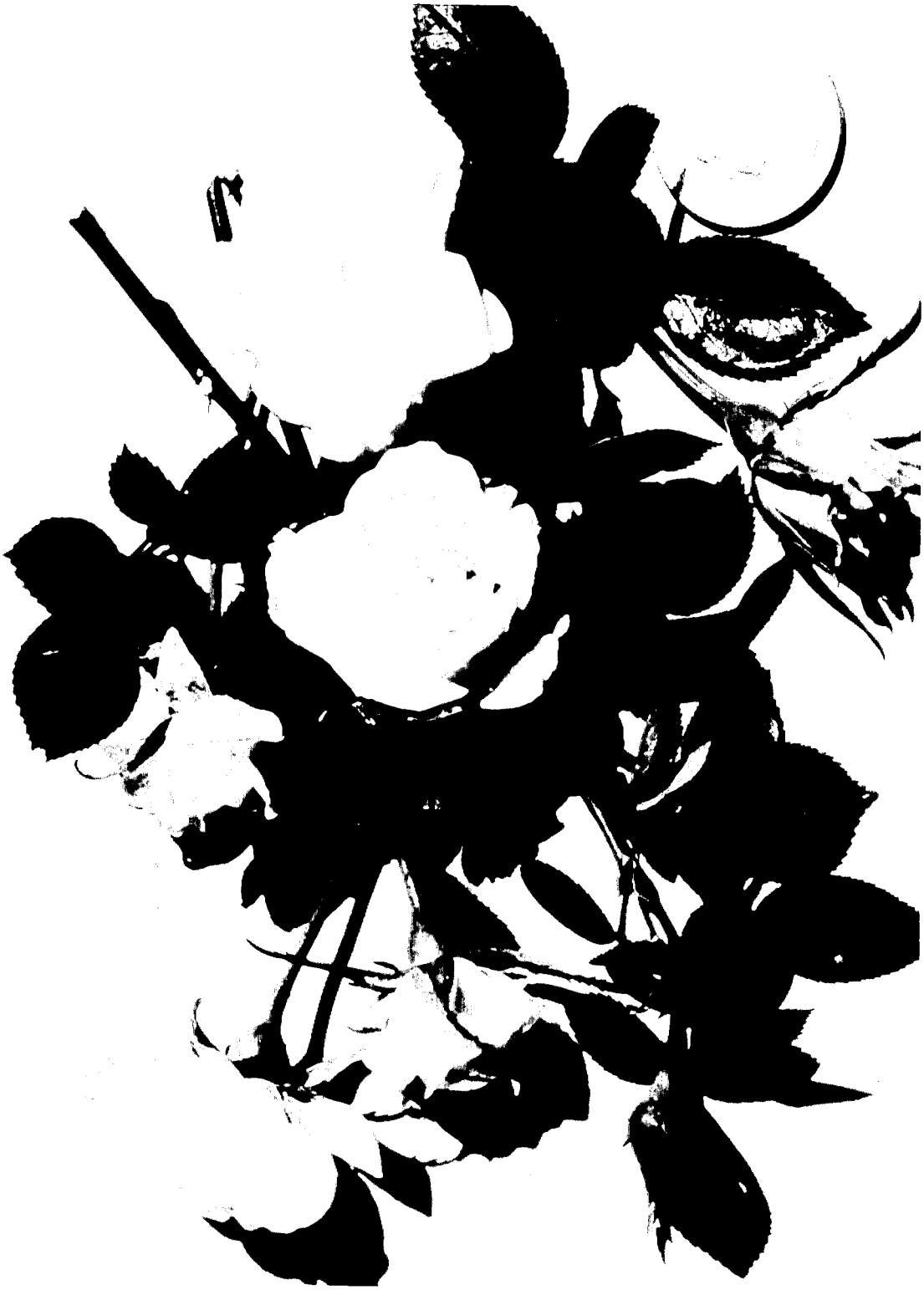

* * * * *